(12) United States Patent
Heneveld

(10) Patent No.: US 9,610,075 B2
(45) Date of Patent: Apr. 4, 2017

(54) SUTURE PASSING DEVICES AND METHODS

(71) Applicant: Scott Heneveld, Whitmore, CA (US)

(72) Inventor: Scott Heneveld, Whitmore, CA (US)

(73) Assignee: Passer Stitch, LLC, Whitmore, CA (US)

( * ) Notice: Subject to any disclaimer, the term of this patent is extended or adjusted under 35 U.S.C. 154(b) by 176 days.

(21) Appl. No.: 14/120,243

(22) Filed: May 8, 2014

(65) Prior Publication Data

US 2014/0296880 A1 Oct. 2, 2014

Related U.S. Application Data

(63) Continuation of application No. PCT/US2012/027782, filed on Mar. 5, 2012.

(51) Int. Cl.
*A61B 17/04* (2006.01)
*A61B 17/06* (2006.01)

(52) U.S. Cl.
CPC ...... *A61B 17/0469* (2013.01); *A61B 17/0482* (2013.01); *A61B 17/0483* (2013.01); *A61B 17/06066* (2013.01); *A61B 2017/0472* (2013.01)

(58) Field of Classification Search
CPC ............ A61B 17/0469; A61B 17/0482; A61B 17/0483; A61B 17/06066; A61B 2017/0472; A61B 2017/00349; A61B 2017/0409; A61B 2017/06052; A61B 17/047; A61B 17/0485; A61B 17/0474; A61B 17/32056

USPC ........ 606/144-148, 139, 232, 224-227, 207, 606/222, 223, 113
See application file for complete search history.

(56) References Cited

U.S. PATENT DOCUMENTS

| | | | |
|---|---|---|---|
| 2005/0165429 A1* | 7/2005 | Douglas | A61B 17/08 606/157 |
| 2005/0251165 A1* | 11/2005 | Vaughan | A61B 17/10 606/153 |
| 2008/0009888 A1* | 1/2008 | Ewers | A61B 17/0401 606/151 |
| 2008/0033232 A1* | 2/2008 | Catanese, III | A61B 17/0401 600/29 |
| 2008/0208221 A1* | 8/2008 | Murray | A61B 17/0469 606/145 |
| 2009/0062816 A1* | 3/2009 | Weber | A61B 17/0469 606/144 |
| 2013/0072948 A1* | 3/2013 | States, III | A61B 17/0483 606/145 |

* cited by examiner

*Primary Examiner* — Melanie Tyson
*Assistant Examiner* — Majid Jamialahmadi

(57) ABSTRACT

A suture passing device includes a notchless tubular needle having a preformed curved shape. One or more cleats are disposed within the needle to help secure suture engaged by the sharp distal tip of the needle and to prevent further bifurcation of the suture. The deformable needle is housed in a channel of a lower jaw having a curved guidepath that approximates the curved geometry of the preformed needle, thereby facilitating the consistent return of the needle to its preformed shape each time the needle exits the channel. A dual needle suture passing device is also provided having a second notchless needle to enable a mattress stitch. Methods of loading a suture onto a notchless needle in a suture passer are also provided.

7 Claims, 8 Drawing Sheets

SUTURE PASSING DEVICES AND METHODS

CROSS REFERENCE TO RELATED APPLICATIONS

This application is a continuation of International Application No. PCT/US2012/027782, with an international filing date of Mar. 5, 2012, which claims priority to U.S. Provisional Patent Application Ser. No. 61/464,578, filed on Mar. 7, 2011.

FIELD OF THE INVENTION

The present invention relates to system, methods, and apparatus for enhancing the advancement and retention of suture through tissue.

BACKGROUND OF THE INVENTION

Suturing apparatus in the past have had an elongate shaft and a low profile distal clamping mechanism to facilitate their use through cannulas in less invasive surgery. These devices have typically included opposing jaws which clamp onto the tissue to be sutured. The end segment of the suture is pre-positioned and secured at the distal end of one jaw member. Beyond the clamping motion, the mechanism for passing a suture between the jaws and through the tissue incorporates a bendable flat needle. The bendable needle advances distally within the jaw member, bringing it in contact with a segment of the suture. The needle has a notch which engages and secures the suture to carry it forward.

This distal advancement of the bendable needle also results in the leading end of the needle to approach and engage a ramp in the jaw member, deflecting the bendable needle in a direction toward the opposing jaw. The bending of the needle requires a high force and results in excess strain on the notched needle component. Fracture and failure of the bendable needle is a concern.

Additionally, capturing suture reliably after being passed through the tissue is also a feature not currently offered by the existing technologies. The ability to throw a horizontal mattress stitch with the desired stitch width without having to remove and reload the instrument is currently an unmet need. Another area of improvement is the need to clamp onto thick tissue and reliably pass suture.

SUMMARY OF THE INVENTION

In accordance with the present invention, structures and associated methods are disclosed which address these needs and overcome the deficiencies of the prior art. The following description includes an example of the methods and devices within the scope of this disclosure. It is also contemplated that combinations of aspects of various embodiments as well as the combination of the various embodiments themselves is within the scope of this disclosure.

In one aspect, a suturing device, or apparatus, comprises of a distal tip and jaw, movable with respect to each other, a bendable, tubular needle housed in distal tip and adapted to carry a suture, and a suture receiver disposed on the opposing jaw. In some embodiments, the device includes a suture driving assembly for positioning a suture in a tissue section, the assembly comprising at least one needle assembly having a tissue piercing end distal to an elongate shaped section, the elongate shaped section having a curvilinear shape, the elongate shaped section being elastically deformable when restrained into a strained state and upon release assumes the curvilinear shape, the suture coupled to the needle assembly; a shaft having a tip with a tissue engaging surface at a distal end, at least one constraining channel and a pivoting jaw with at least one retrieving channel, each of which having an opening at the tissue engaging surface; such that when the elongate shaped section of the needle assembly is in the restraining portion, the elongate shaped section is deformed into the strained state and when the elongate shaped section advances through the guide segment portion, the elongate shaped section assumes the curvilinear shape, upon continued advancement the elongated shaped section exits through the opening of constraining channel in the curvilinear shape; a suture retriever assembly located in the pivoting jaw.

The needle assembly as well as the number of needle assemblies can vary depending upon the type of suture stitch required. For example, the device can include a single needle assembly having a single shaped section or multiple shaped sections. In alternate variations, the assembly comprises two or more needle assemblies; the needle assemblies as well as the shaped portions used in any particular suture driving mechanism need not have the same shape. Instead, a single suture driving assembly can use needle assemblies of differing shapes at the same time; however, the spacing and relation of the constraining channel and the retrieval channel shall be adjusted to accommodate a particular shape and configuration of a particular needle assembly.

The suture devices and methods described herein can include a needle assembly comprising a needle lumen extending through at least the tissue piercing end and where the suture is removably positioned on the distal end of the needle; in another variation, a single suture can be affixed at both ends to a pair of needle assemblies where the needle assemblies comprise two shaped sections with each having a tissue piercing end.

Sutures used in the present devices and methods can be front loaded into a needle assembly; as a result, a suture retriever assembly can remove the suture from the needle assembly via a front portion of the needle assembly; in one example, the suture retriever assembly comprises at least one pawl member that reduces an opening of the retrieving channel to less than a size of the needle assembly and suture, where the pawl member in a first position allows the needle assembly and suture to move in a first direction and prohibits suture movement in a second direction.

The devices described herein can be combined with various other medical implements to aid in the suturing of tissue.

In another variation, a suture driving assembly for placing suture in a tissue section can include a first needle assembly having a tissue piercing end distal and being elastically deformable when restrained into a strained state and upon release assumes the curvilinear shape; a suture exterior to the needle assembly and having at least one end front-loaded onto the distal end of a needle of a first tissue piercing portion of the first needle assembly; a cleat is supported in the needle lumen and extends from the distal end of the needle lumen to engage the suture, thus preventing the bifurcation of the suture from sliding down the shaft of the needle; a shaft having a tissue engaging surface at a distal end, at least one constraining channel, and a pivoting jaw with at least one retrieving channel, each of which having an opening at the tissue engaging surface; where the constraining channel extends through the shaft tip and comprises at least a restraining portion having a profile to maintain the needle assembly into the strained state and a guide segment portion adjacent to the constraining channel opening and having a profile to release needle assembly into the curvilinear shape when advanced there through and upon continued advancement the needle assembly exits the opening of the constraining channel in the curvilinear shape; a suture retriever assembly located in the needle retrieving channel and comprising a pawl mechanism, where the pawl mechanism interferes with the front loaded suture and needle assembly when advanced therein, where rearward movement of the front loaded suture and needle assembly causes the pawl to engage the suture to retain the suture within the needle retrieving channel.

In another variation, the method may further include advancing a plurality of needle assembly pairs, where each needle assembly pair is coupled to an end of a suture and where each needle assembly advances from a respective constraining channel into a respective guide segment, where the guide segment permits the shaped section of the respective needle assembly located therein to revert to the curvilinear shape prior to leaving the respective guide segment and enter the wall of the organ; and where the plurality of needle assemblies move through the curvilinear shape so that the tissue piercing distal end of each needle assembly pair re-enter the main body at a respective retrieving channel.

As described above, the method optionally includes the use of front-loaded sutures. Such sutures allow for securing the suture in the retrieving channel by advancing the needle assembly and suture against a pawl mechanism such that the pawl mechanism compresses the suture to retain the suture while allowing the needle assembly to be withdrawn back into the constraining channel.

In certain variations, the suture driving assembly can be used to drive a needle without any suture. In such a case, the needle may be left within the tissue (to be removed later, to be absorbed by the native tissue, or for permanent placement.) Accordingly, needle driving assemblies having the same or similar structures disclosed herein are within the scope of this disclosure.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
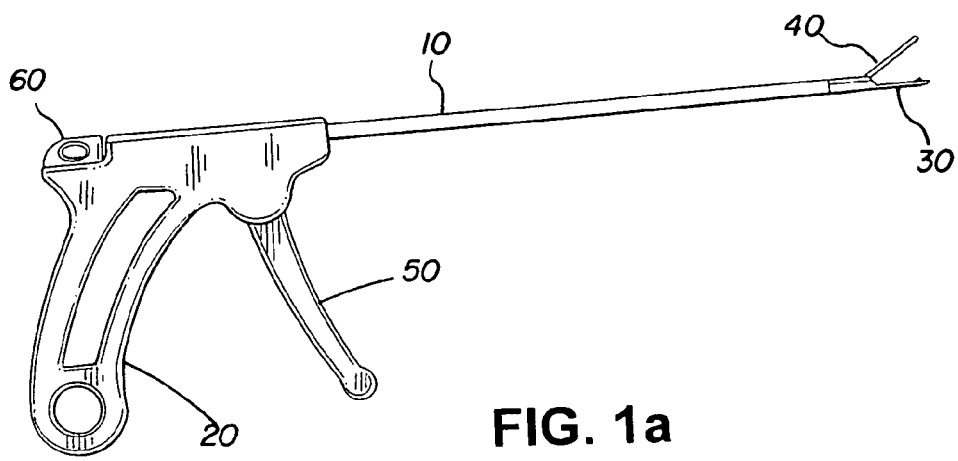
FIGS. 1A-1C show side views of a preferred embodiment of a suture passing device in various stages of deployment.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention relates generally to systems and methods for the driving of a needle or suture through or into body tissue (typically, the needle will be affixed to a suture that remains in the tissue) using a cannula, introducer or other minimally invasive means. The methods and devices described herein can be used in any number of medical procedures, including but not limited to, approximating tissue (e.g., bring separated tissue together), ligating tissue (e.g., encircling or tying off), and fixating of tissue (attaching tissue to another structure or different tissue).

The term "endoscopy" encompasses arthroscopy, laparoscopy, hysteroscopy, among others, and endoscopic surgery involves the performance of surgical procedures within a patient's body through small openings as opposed to conventional open surgery through large incisions.

Both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Figure 1B:
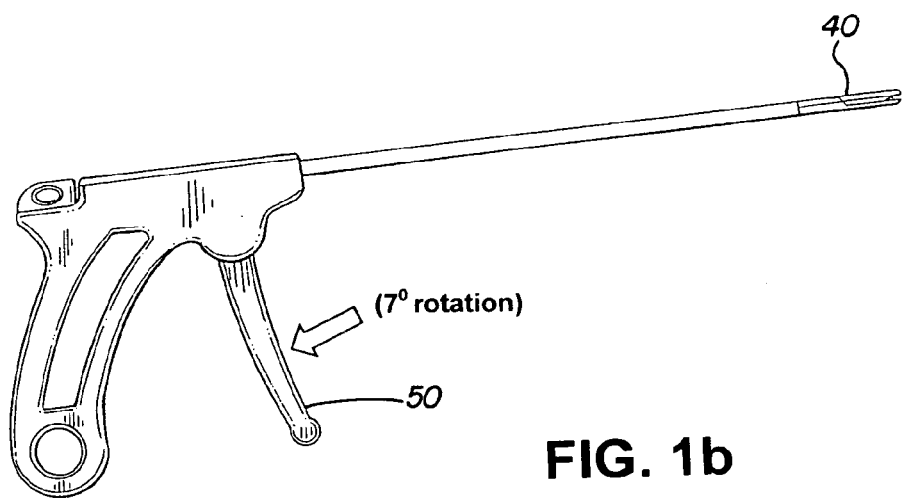

Referring now to the images where like elements are represented by like reference numerals. FIG. 1A illustrates a suture passing device, or instrument, of the present invention having an elongated tubular body 10, a hand grip 20, a tip 30, a jaw 40, an actuator 50 and a needle assembly 60. With actuator 50, a surgeon may seize and maintain tissue by movement of jaw 40 against tip 30 as shown in FIG. 1B. Using actuator 50, a surgeon may also deploy needle assembly 60 with tubular needle 70 carrying a suture 71 through tissue, as described below.

Figure 2A:
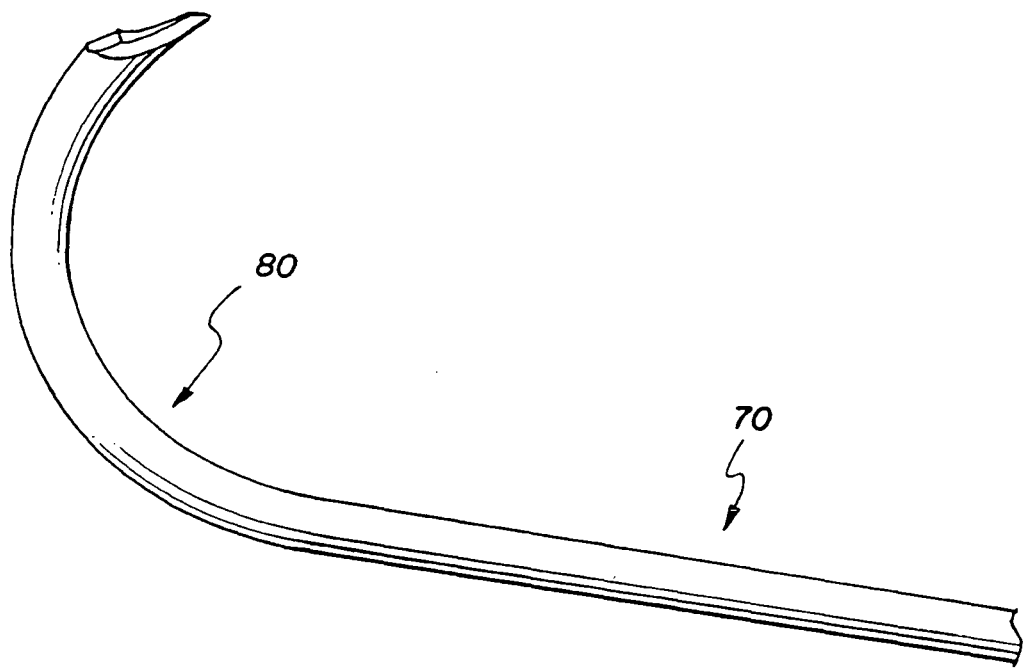
FIG. 2A is a side view of a preferred notchless tubular needle having a preformed memory shape.
Figure 2B:
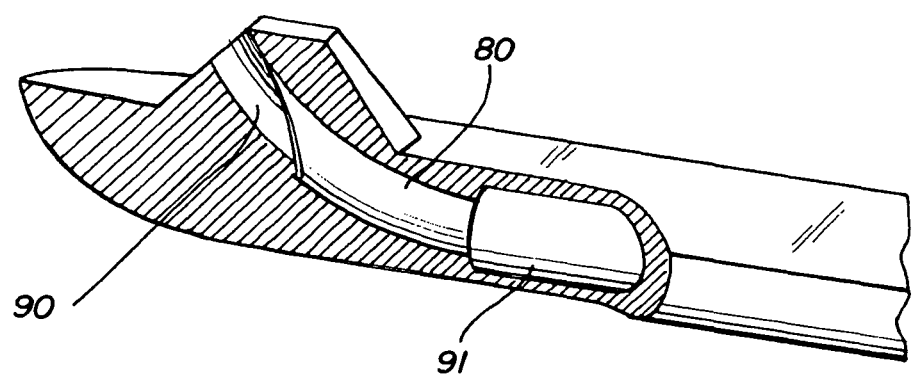
FIG. 2B is a side view of a preformed tubular needle in a sheathed, constrained state.

FIG. 2A shows a preferred notchless tubular needle 70 in its natural state. As used throughout the specification, "notchless" shall refer to the absence of notches, slots, eyelets, or other such transverse openings for receiving suture as typically formed in needles of prior art suture passers. The distal end of the needle 80 is formed in a non-straight geometry. FIG. 2B shows a tubular needle 70 with the formed end 80 sheathed in a constraining channel 91. The channel for the needle also includes a curvilinear portion 90, or guide-path, that approximates the same geometry curve as the distal end of the tubular needle 80, thereby facilitating the consistent return of the needle 70 its preformed curved shape each time the needle 70 exits the channel. The constrained state tubular needle 70 contained in the needle assembly 60 is loaded into the handle end of the tubular body 10 and advanced through a track in the tubular body 10.

Figure 1C:
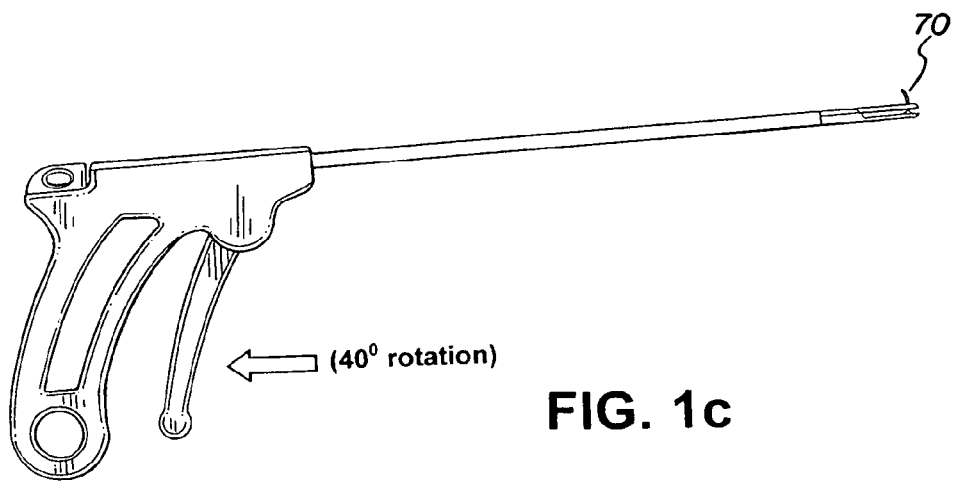

FIG. 1A illustrates a hand grip 20 and actuator 50 that provide articulation of jaw 40 relative to tip 30. The actuator 50 may be coupled to a return spring that biases the actuator 50 in the open position as seen in FIG. 1A. A surgeon may rotate actuator 50 approximately five to ten degrees, and preferably seven degrees, toward hand grip 20 to close jaw 40, as seen in FIG. 1B. A surgeon may then rotate actuator 50 approximately an additional thirty to forty degrees, and preferably thirty four degrees, towards hand grip 20 to activate tubular needle 70, extending it to its natural state 80, seen in FIG. 1C. The initial additional actuator rotation could require a significant resistance from a spring in the handle mechanism. This significant resistance on the actuator 50 acts as an indicator for the operator to know the tubular needle 70 is beginning to be deployed. Releasing the actuator 50 to its resting, open position returns tubular needle 70 to its constrained state 90 and then disengages jaw 40 to the open position.

Figure 3A:
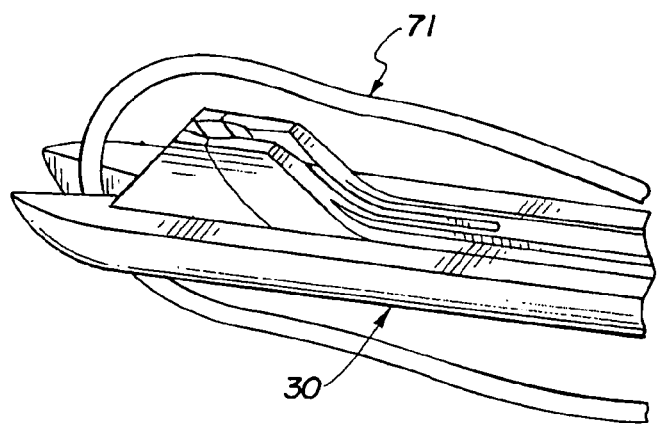
FIG. 3A is a side view of the preferred device's tip and suture prior to loading.
Figure 3B:
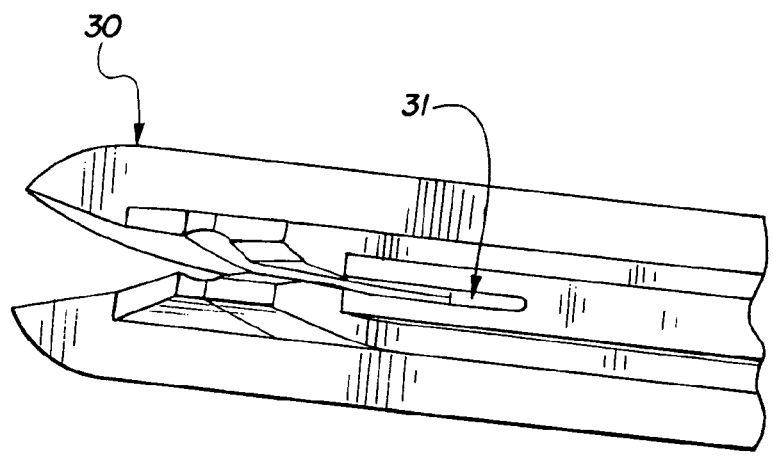
FIG. 3B is a perspective view of the tip with slot formed in a lower jaw.

In FIG. 3A a loop of suture 71 is loaded into distal end of tip 30 with slot 31, seen in FIG. 3B. The slot 31 allows spring action for gripping the loop of suture 71 when the loop of suture is pulled into the tip 30. In one embodiment, shown in FIG. 3C, tubular needle 70 pierces the loop of suture 71 and creates a bifurcation 72 in the suture. When additional force is applied to the suture, the bifurcation 72 will advance along the shaft of the needle. To prevent the bifurcation 70 from advancing along the shaft of the needle, a prong cleat 73, illustrated in FIG. 4A is positioned to pierce the loop of suture 71 loop in second location. The pierce of the prong cleat may partially engage the thickness of the suture or create a second bifurcation 74 in the suture. The prong cleat 72 is a wire rod or tube housed within the lumen of the tubular needle with a sharp distal tip 73, shown in FIG. 4C, that slightly extends from the lumen of the tubular needle 70, as seen in FIG. 4B. The two piercing objects at different locations in the suture act in conjunction to stabilize the suture from advancing along the shaft of the needle.

Figure 3C:
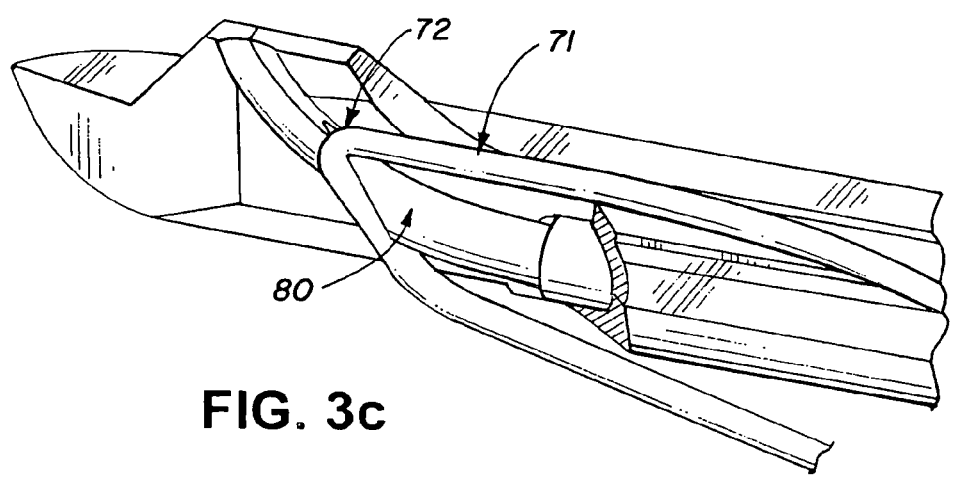
FIG. 3C is a perspective view of the tip, tubular needle, and suture.
Figure 4A:
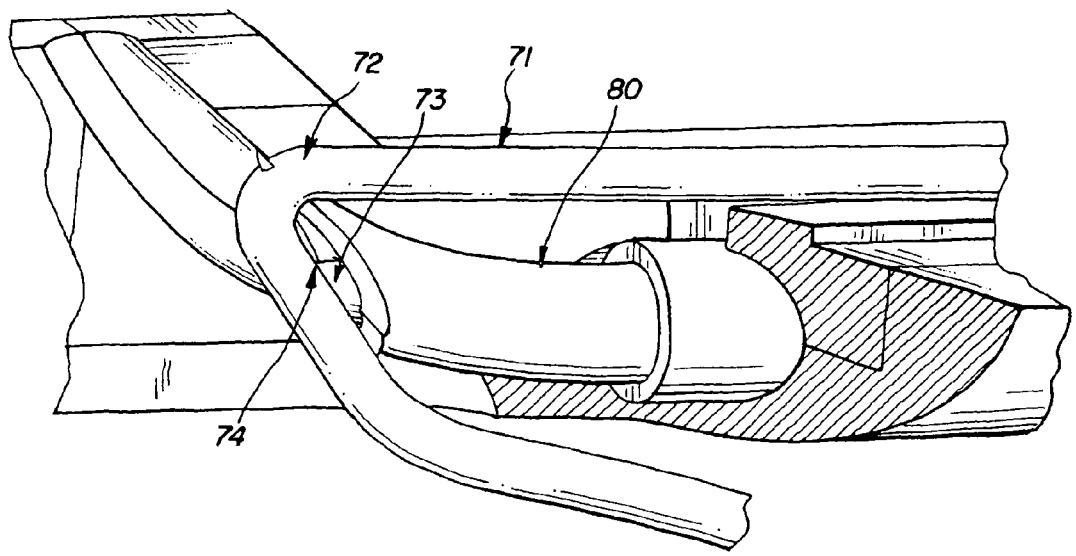
FIG. 4A is a perspective view of the tip, tubular needle, cleat, and suture.
Figure 4B:
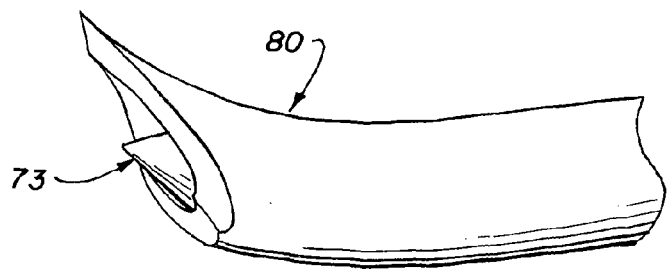
FIG. 4B is a perspective view of the device's tubular needle and prong cleat.
Figure 4C:
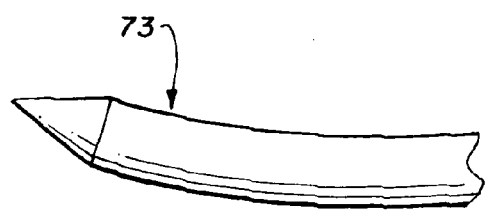
FIG. 4C is a perspective view of the device's prong cleat.
Figure 5A:
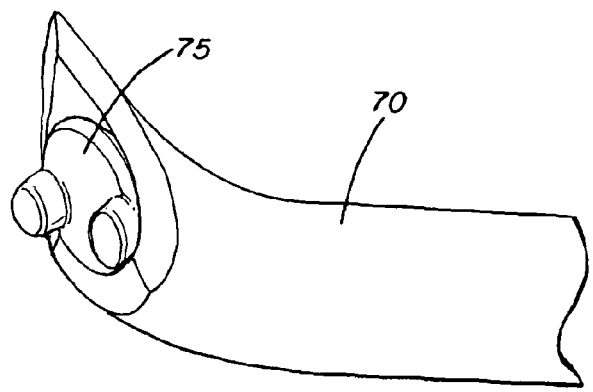
FIG. 5A is a perspective view of the device's tubular needle and lateral post cleat.
Figure 5B:
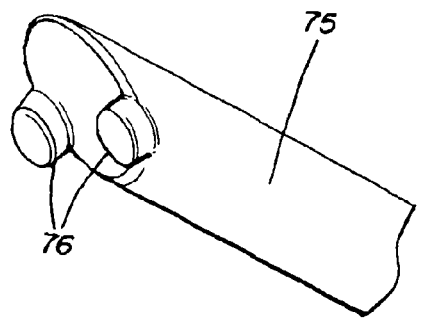
FIG. 5B is a perspective view of the device's lateral post cleat.
Figure 5C:
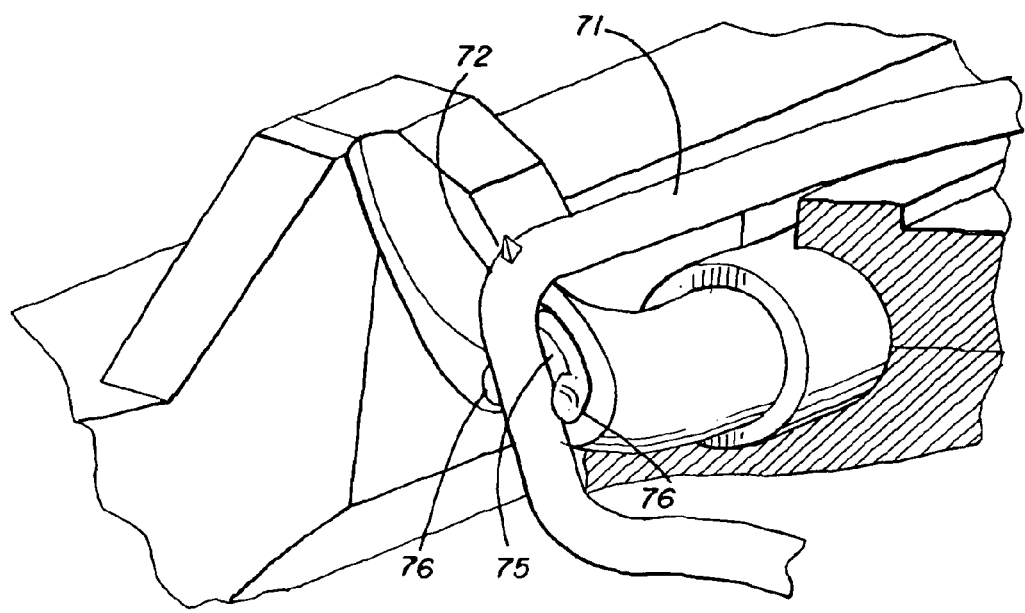
FIG. 5C is a perspective view of the device's tip, tubular needle, cleat, and suture.

In another embodiment, shown in FIG. 3C, tubular needle 70 pierces the loop of suture 71 and creates a bifurcation 72 in the suture. When additional force is applied to the suture, the bifurcation 72 will advance along the shaft of the needle. To prevent the bifurcation 72 from advancing along the shaft of the needle, a lateral post cleat 75, illustrated in FIG. 4A is positioned to engage the bifurcated section of the suture, FIG. 5C. The body of the lateral post cleat 75 is housed inside the lumen of the tubular needle 70. Tension on the loop of suture 71 pulls the bifurcated legs of the suture against the lateral post 76, preventing the suture from sliding down the shaft of the needle.

Figure 6A:
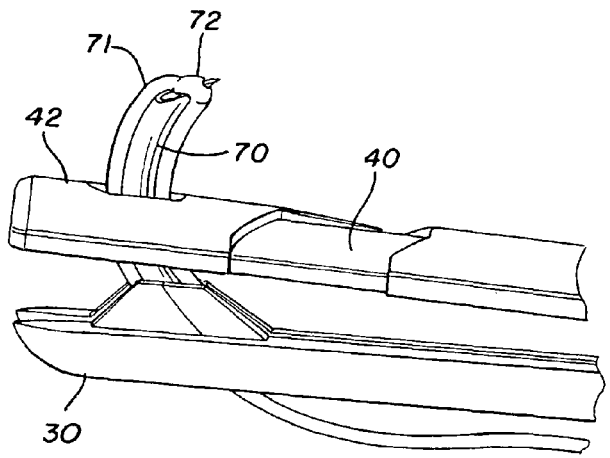
FIG. 6A is a partial side view of the tubular needle extended to carry the suture through the aperture of the jaw and pawl.
Figure 6B:
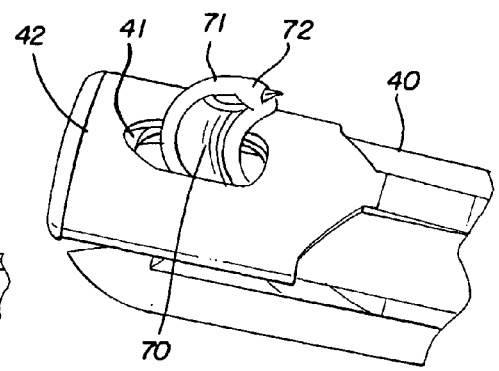
FIG. 6B is a perspective view of the tubular needle extended to carry the suture through the aperture of the jaw and pawl.
Figure 6C:
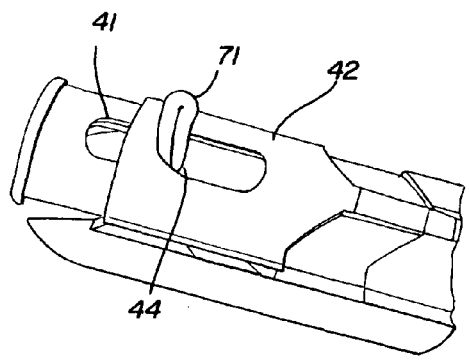
FIG. 6C is a perspective view of the suture captured by the pawl.
Figure 6D:
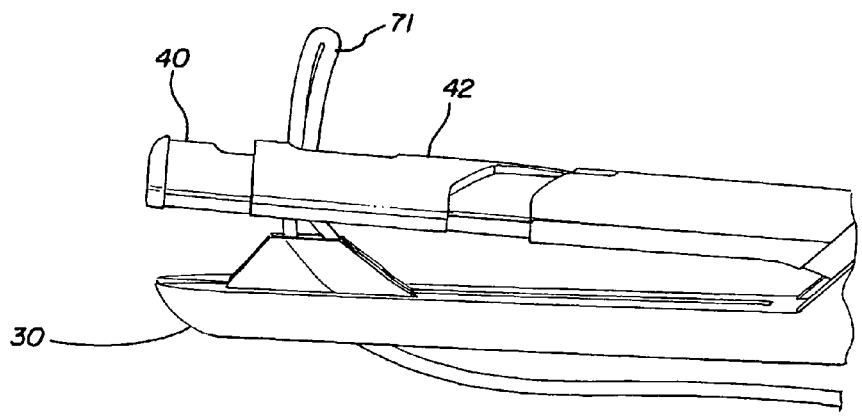
FIG. 6D is a side view of the suture captured by the pawl.

FIG. 6B shows an aperture 41 in jaw 40 that tubular needle 70 and suture 71 pass through, as seen in FIG. 6A. A retractable pawl 42 is sideably positioned on jaw 40. Retractable pawl 42 includes a window 43 that aligns with aperture 41 when extended forward in the open position. With tubular needle 70 and suture 71 deployed within aperture 41 by rotation of the actuator 50, the retractable pawl is then actuated to a reward position. The mechanism to actuate reward motion of the retractable pawl 42 may include a spring bias to provide a relatively constant load of the retractable pawl 42 against the deployed tubular needle 70 and suture 71. Upon release of the actuator 50, a spring in the actuator mechanism returns the tubular needle 70 to the constraining channel 90. The spring bias of the retractable pawl 42 allows the tubular needle to return, yet maintains a grip on the suture 71 and pulls it in a reward movement to become captured in between the proximal edge 44 of the aperture 41 in the jaw 40 and distal edge of pawl window 43, as is shown in FIGS. 6C and 6D. Complete release of the actuator 50 disengages the jaw 40 to the open position, thus completing the passage of suture through the tissue.

Figure 7A:
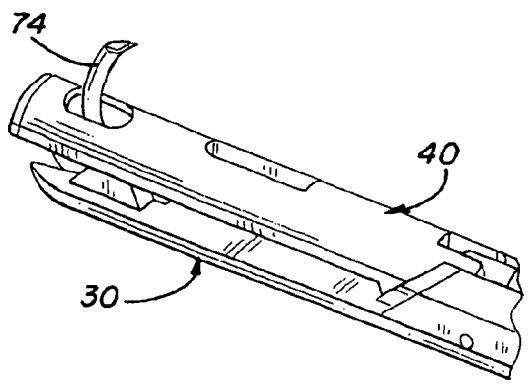
FIG. 7A is a perspective view of a preferred embodiment having two tubular needles and jaw.

In some variations, the suture passing device may be composed to have two or more tubular needles 70. In one embodiment, the suture passing device can throw more than one segment of suture through tissue simultaneously. The segments of suture being passed by multiple tubular needles may be attached to form a continuous loop of suture, thus enabling the formation of a desired suture pattern, i.e. horizontal mattress stitch. FIG. 7A shows a left tubular needle 74 and a right tubular needle 75 after being simultaneously released to their natural states 80. In another embodiment, the device may throw two or more tubular needles 70 through tissue sequentially.

Figure 7B:
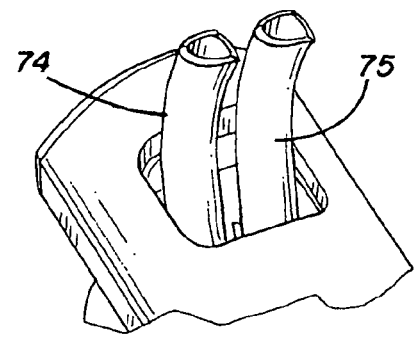
FIG. 7B is a perspective view of the left tubular needle extended in the jaw.
Figure 7C:
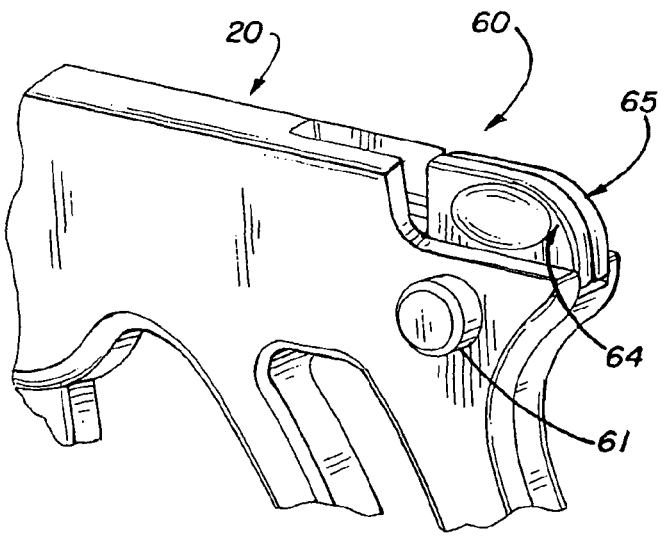
FIG. 7C is a side view of the device's hand grip, toggle switch and needle assemblies.

The segments of suture being passed by multiple tubular needles may be attached to form a continuous loop of suture, thus enabling the formation of a desired suture pattern, i.e. horizontal mattress stitch. The handle mechanism could be configured to deploy the left needle assembly 64 and right needle assembly 65 independently. FIG. 7C shows the handle mechanism with a switch 61 to toggle and engage one needle assembly at a time in the drive track 60. Suture could be loaded to the tips of both needle assemblies (as described above) before entering the device down the cannula. With the switch 61 toggled to engage the left needle assembly 64, the jaw could be actuated to grasp a desired location of tissue and the left tubular needle 74 deployed to pass suture and capture suture in a first tissue location. FIG. 7B shows a left tubular needle 74 released to its natural state 80 (suture is not shown in image).

Figure 7D:
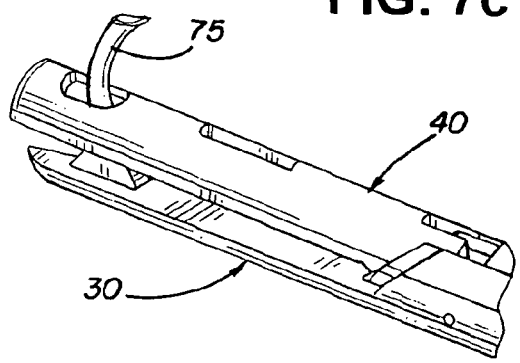
FIG. 7D is a perspective view of the right tubular needle extended in the jaw.

Fully releasing the actuator 50 returns the left tubular needle 74 to its constrained state 90 and disengages jaw 40. The suture passing instrument may then be repositioned to a second desired tissue location. A surgeon could then select right needle assembly 65 by toggling the needle track 60 on the instrument's body 10, as seen in FIG. 7C. With the switch 61 toggled to engage the right needle assembly 65, the jaw could be actuated to grasp a second desired location of tissue and the right tubular needle 75 deployed to pass suture and capture suture in a second tissue location. FIG. 7D shows a right tubular needle 75 released to its natural state 80 (suture is not shown in image). Fully releasing the actuator 50 returns the right tubular needle 75 to its constrained state 90 and disengages jaw 40 from tissue. The suture passing instrument may then be removed from the cannula to expose the two ends of the suture.

Figure 8A:
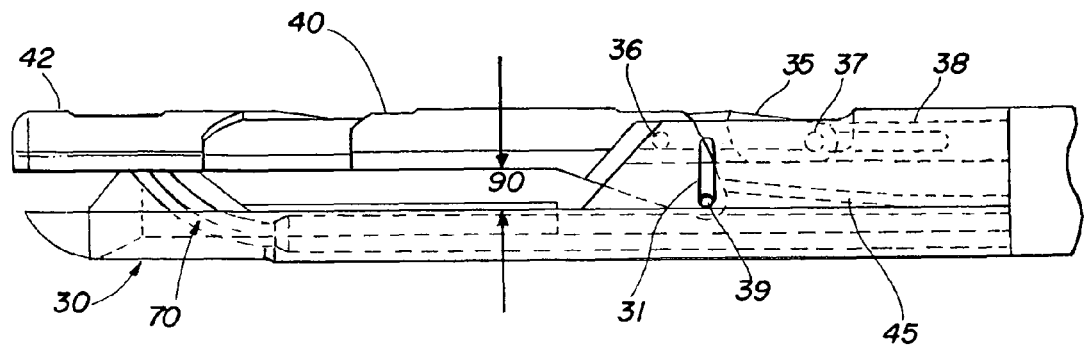
FIG. 8A is a side view of tip with slot and floating pivot in the collapsed state.
Figure 8B:
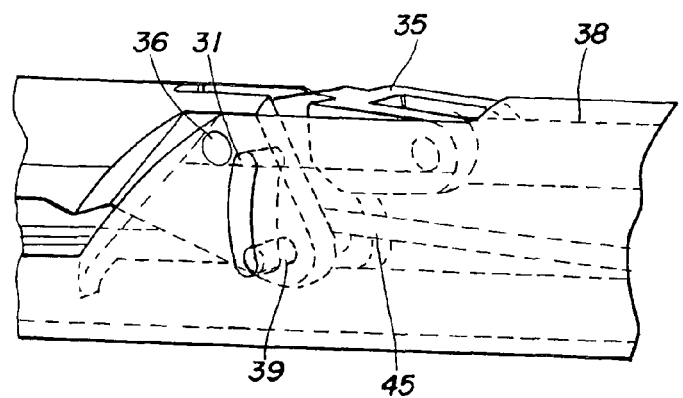
FIG. 8B is a perspective view mechanism for the floating pivot.
Figure 8C:
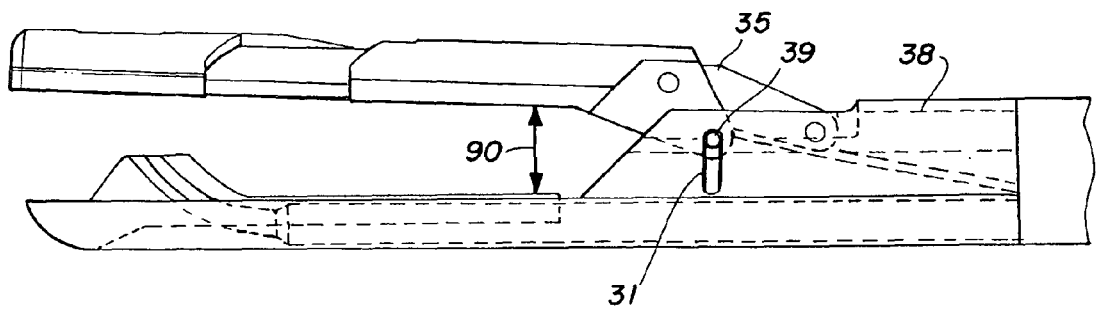
FIG. 8C is a side view of tip with slot and floating pivot in the expanded state.

In yet another embodiment, the device described above includes floating a pivot mechanism as shown in FIGS. 8A-C to facilitate a lower profile when the jaws are separated. The jaw 40 includes a pivot interface 36 with linkage 35. At the opposite end of linkage 35 is another pivot interface 37 that joins linkage 35 and drive rod 38. The tip 30 includes a slot 31 in which a pin 39 slides within. The pin 39 is fixed to jaw 40. Axial movement of drive rod 38 in relation to the tip 30 causes jaw 40 to rotate about pin 39 in relationship to the tip 30. A leaf spring 45 exerts a load against the pin 39 in a direction to bias the pin against the lower end of slot 31, thus resulting in the jaw 40 in a collapsed state as shown in FIG. 8A. The gap 90 between the inner surfaces of the tip 30 and jaw 40 is minimized. The collapsed state is advantageous for providing a minimum profile for advancing the device through a cannula. The leaf spring segment 45 may be an integral part of the pawl 42.

When the tip 30 and jaw 40 are positioned unto tissue, advancement of the drive rod 38 causes the jaw 40 to rotate about pin 39 to clamp onto the tissue. The resisting force of the tissue to compression between tip 30 and the jaw 40 causes a force on the inner surface of the jaw 40. If the force on the inner surface of the jaw 40 exceeds the force of the leaf spring 45 to hold the pin 39 against the lower end of slot 31, the pin will ride up the slot 31, and effectively increase the gap 90 between the inner surfaces of tip and the jaw 40, as shown in FIG. 8C. To increase the gap 90 at the axillia acts to distribute the clamp force along the length of the jaw 40. The distribution of clamp force enables the distal end of jaw 40 to achieve a position in closer proximity to tip 30.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what incorporates the essential idea of the invention.

What is claimed is:

1. A suture passing device, comprising:
   a suture;

a deformable needle comprising;
  a primary member including a tissue piercing end and a distal opening, the tissue piercing end is distal to an elongate shaped section, the elongate shaped section having a curvilinear shape, the elongate shaped section being elastically deformable into a strained state and upon release to an unstrained state assumes the curvilinear shape;
  a cleat member housed at least partially within the distal opening of the primary member and configured to protrude distally outward from the distal opening;
a first jaw defining an axis and including a channel having a curved channel geometry that approximates the curvilinear shape of the deformable needle, the channel housing the deformable needle when retracted and providing an exit of the deformable needle to facilitate the deformable needle returning to its curvilinear shape upon exit;
a second jaw movable with respect to the first jaw for holding tissue to be sutured;
and during a surgical procedure, the tissue piercing end of the deformable needle pierces the suture while the cleat member releasably engages the suture to carry the suture through the tissue and to inhibit bifurcation of the suture engaged by the tissue piercing end of the deformable needle.

2. The device of claim 1, wherein the cleat member has a sharp tip for engaging the suture.

3. The device of claim 1, wherein the cleat member comprises a first cleat, the device further comprising a second cleat disposed within the needle primary member and configured to protrude out from the distal opening of the primary member.

4. The device of claim 1, wherein the second jaw defines an aperture through which the suture may be passed, the device further comprising:
  a pawl coupled to the second jaw, the pawl defining a window and being movable with respect to the second jaw such that the window is movable between a first position in which the window substantially overlaps the aperture and a second position in which the window does not substantially overlap the aperture, thereby causing the suture to be pinched between window and aperture.

5. The device of claim 1, wherein the first jaw comprises a slot engaging a pin secured to the second jaw as a means for the second jaw to movably pivot with respect to the first jaw so at to remain substantially parallel to the first jaw when the second jaw is moved toward the first jaw when being clamped over tissue.

6. The device of claim 1, wherein the needle comprises a first needle, the device further comprising:
  a second needle disposed adjacent to the first needle.

7. The device of claim 6, further comprising:
  an actuator operatively coupled to the first needle and the second needle; and
  a switch to toggle operative connection of the actuator to either the first needle or the second needle.

* * * * *